United States Patent [19]

Skorianetz et al.

[11] 4,014,905
[45] Mar. 29, 1977

[54] ESTERS OF CERTAIN TETRAMETHYL AND PENTAMETHYL-1-OXA-SPIRO [4-5] DECAN-6-OLS WITH CERTAIN ALKANOIC ACIDS

[75] Inventors: Werner Skorianetz, Geneva; Walter Renold, Onex; Gunther Ohloff, Bernex; Karl-Heinrich Schulte-Elte, Onew, all of Switzerland

[73] Assignee: Firmenich S.A., Geneva, Switzerland

[22] Filed: Oct. 23, 1975

[21] Appl. No.: 625,452

Related U.S. Application Data

[63] Continuation-in-part of Ser. No. 542,072, Jan. 17, 1975, abandoned.

[30] Foreign Application Priority Data

Feb. 4, 1974 Switzerland .................. 1488/74
June 7, 1974 Switzerland .................. 7776/74
July 30, 1975 Switzerland .................. 9920/75

[52] U.S. Cl. .................. 260/347.4; 260/347.8; 252/522; 426/536; 131/17 R

[51] Int. Cl.$^2$ .................. C07D 307/94
[58] Field of Search .................. 260/347.4, 347.8

[56] References Cited

OTHER PUBLICATIONS

Nakatani et al., Tetrahedron Letters, No. 24, pp. 1995-1998, (1969).

*Primary Examiner*—Henry R. Jiles
*Assistant Examiner*—Bernard Dentz
*Attorney, Agent, or Firm*—Pennie & Edmonds

[57] ABSTRACT

Spirane derivatives, most of them are new, useful as odor-modifying ingredients for manufacturing perfumes and perfumed products, and as flavor-modifying ingredients for the manufacture of artificial flavors of for flavoring foodstuffs, animal feeds, beverages, pharmaceutical preparations and tobacco products.

Process for preparing said spirane derivatives.

7 Claims, No Drawings

ESTERS OF CERTAIN TETRAMETHYL AND PENTAMETHYL-1-OXA-SPIRO [4-5] DECAN-6-OLS WITH CERTAIN ALKANOIC ACIDS

CROSS REFERENCE TO RELATED APPLICATION

This application is a continuation-in-part of our earlier filed and copending application, Ser. No. 542,072, filed Jan. 17, 1975 and now abandoned.

SUMMARY OF THE INVENTION

The invention relates to novel spirane derivatives of formula

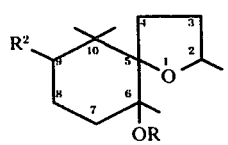
(I)

wherein the symbol R represents an acyl radical containing from 1 to 6 carbon atoms and $R^2$ represents a hydrogen atom or methyl radical.

The invention further relates to the use of spirane derivatives of formula

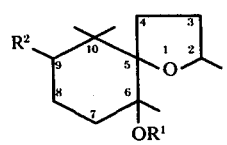
(II)

wherein the symbol $R^1$ represents a hydrogen atom or an acyl radical containing from 1 to 6 carbon atoms and $R^2$ represents a hydrogen atom or methyl radical, as odour- and flavour-modifying ingredients.

The invention also relates to 2,6,10,10-tetramethyl-1-oxa-spiro [4.5]dec-3-en-6-ol, 6,7-epoxy-2,6,10,10-tetramethyl-1-oxa-spiro[4.5]decane, 2,6,9,10,10-pentamethyl-6,7-epoxy-1-oxa-spiro[4.5]dec-3,6-diene, 2,6,9,10,10-pentamethyl-6,7-epoxy-1-oxa-spiro[4.5]-dec-3-ene and 2,6,9,10,10-pentamethyl-6,7-epoxy-1-oxa-spiro[4.5]decane useful as intermediate compounds for the preparation of compounds (II).

The invention further relates to a perfume or a flavour-modifying composition comprising as one of its active ingredients a spirane derivative of formula (II), as set forth hereinabove.

The invention finally relates to a process for preparing a spirane derivative of formula (II), said process comprising A. cyclizing a compound of formula

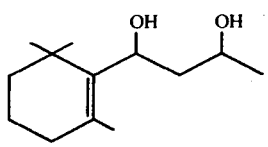
(III)

to give a compound of formula

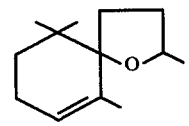
(IV)

epoxidizing the compound (IV) thus obtained to give a compound of formula

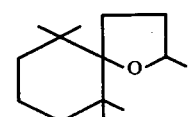
(V)

reducing the above epoxide and, if required, esterifying the obtained reduction product; or B. epoxidizing a compound of formula

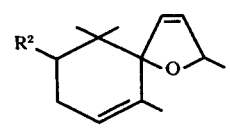
(VI)

to give a compound of formula

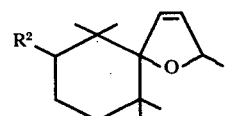
(VII), subjecting the above compound to a catalytic hydrogenation to give a compound of formula

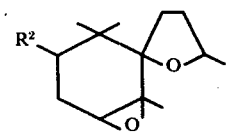
(V)

reducing the above epoxide and, if required, esterifying the obtained reduction product; or C. reducing the compound (VI) described sub letter B to give a compound of formula

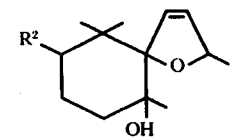
(VIII), subjecting the above compound to a catalytic hydrogenation and, if required, esterifying the obtained hydrogenation product; or D. epoxidizing and subsequently subjecting to an acidic treatment a compound of formula

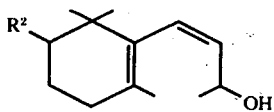

to give a compound of formula

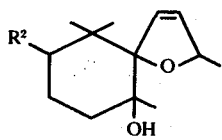

subjecting the above compound to a catalytic hydrogenation and if required esterifying the obtained hydrogenation product.

BACKGROUND OF THE INVENTION

During the last decade, an increasing interest has been developed in the art of perfumery for materials possessing a woody-type odour. One of the consequences of such an increase of interest consisted to promote a drastic shortage of naturally occurring materials traditionally used in the art for the reconstitution of woody-type olfactive notes.

Patchouli oil is an example of this type of material. This essential oil is well known in the art for its typical woody and balsamic fragrance, at the same time spicy, sweet and herbaceous. The said essential oil is moreover noteworthy for its particularly tenacious and powerful odour, and consequently is very broadly used in perfumery, particularly in fine perfumery, for the preparation of various compositions such as those having an oriental, woody, "chypre" or "fougere" character for example.

It has been surprisingly found that it is now possible to faithfully reproduce certain typical nuances of the odoriferous character of natural patchouli oil, by using spirane derivatives of formula (II).

2,6,10,10-Tetramethyl-1-oxa-spiro[4.5]decan-6-ol for example, when used in a perfume or in a perfumed product, imparts thereto an elegant and harmonious woody and balsamic olfactive note similar to that obtained by the use of patchouli oil itself.

It is known in the art that the fragrance of a given essential oil results from the combination of the different odours of each individual constituent of the said oil and can vary depending on the origin or on the purity of the said natural essential oil. It is therefore very rare to find that a single compound can by itself totally reproduce the full character of an essential oil.

In certain cases however, patchouli oil can be advantageously replaced by the spiranic compounds (II) whenever it is desired to impart to a perfume or a perfumed product the woody and balsamic note typical of the said essential oil.

PREFERRED EMBODIMENTS OF THE INVENTION

We have surprisingly found that the compounds of formula (II) are characterized by their woody-type odour. Ester derivatives of formula (II) differ from the corresponding alcohols by a greater diffuseness associated with an amber-like, balsamic, flowery and even herbaceous note.

Spirane derivatives (II) are particularly useful in fine perfumery as well as for the preparation of perfumed products such as soaps, detergents, household materials or cosmetic preparations for example. The compounds of formula (II), particularly 2,6,9,10,10-pentamethyl-1-oxa-spiro[4.5]decan-6-yl acetate, can also develop fruity sulfury organoleptic notes which are reminiscent of the character developed by blackcurrent fruits.

When compounds (II) are used as ingredients for the preparation of perfume compositions, the proportions used may vary within a wide range and are generally comprised between about 1 and 10% (parts by weight) of the said composition. Higher proportions, in some instances up to 50 or even 80%, can also be used when compounds (II) are used as reinforcing agents in base perfume compositions. Lower proportions of the order of about 0.01% to 0.1% are used whenever the compounds of formula (II) are employed to perfume products as soaps or detergents.

Owing to their particular organoleptic properties, compounds (II) can also be used in the flavour industry as ingredients for the preparation of artificial flavours or for the aromatization of foodstuffs, animal feeds, beverages, pharmaceutical preparations and tobacco products.

Depending on the nature of the products in which they are incorporated, compounds (II) can enhance or develop various gustative notes such as woody, amber-like, earthy and in certain cases slightly flowery notes, or even notes reminiscent of that of cedar wood oil. Compounds (II) are therefore particularly appreciated for the preparation of artificial flavours such as citrus fruits or even mushroom flavours wherein the woody and earthy gustative note is often requested.

Compounds (II) can also advantageously be used for flavouring tobacco or tobacco products by imparting thereto a woody, amber-like and cedar wood-like note reminiscent of that of oriental tobaccos.

The woody and earthy note typical of certain compounds (II) is also appreciated for the aromatization of infusions or decoctions such as tea, camomile or verbena for example.

The term "foodstuff" is here used broadly and includes also products such as coffee, tea or chocolate.

Depending on the nature of the flavoured material or on the organoleptic effects desired, the proportions used may vary within a wide range. When compounds (II) are used as ingredients for flavouring foodstuffs or beverages for example, interesting effects may be achieved by the use of proportions comprised between about 0.01 and 20 ppm, based on the weight of the flavoured material. For the aromatization of tobacco or tobacco products the proportions used are often comprised between 0.5 and 500 ppm, preferably between 30 and 50 ppm.

When compounds (II) are used for the preparation of artificial flavours, they are generally used in proportions up to 20%, or even more, of the weight of the said composition.

In all cases, depending on the olfactive or gustative effects desired, smaller or higher proportions than those given above can also be used.

Most of the spirane derivatives of formula (II) which can be used in accordance with the present invention are novel compounds, these latter ones being represented by general formula (I).

In contradistinction, 2,6,10,10-tetramethyl-1-oxa-spiro[4.5]decan-6-ol is a prior known compound, the preparation thereof being described in Tetrahedron Letters 1969, 1995. It has to be noted however that the above reference does not mention any organoleptic properties of said alcohol nor does it suggest its use as perfuming or flavouring ingredient.

Also new are the following spirane derivatives: 2,6,10,10-tetramethyl-1-oxa-spiro[4.5]dec-3-en-6-ol, 6,7-epoxy-2,6,10,10-tetramethyl-1-oxa-spiro[4.5-]decane,2,6,9,10,10-pentamethyl-1-oxa-spiro[4.5-]deca-3,6-diene, 2,6,9,10,10-pentamethyl-6,7-epoxy-1-oxa-spiro[4.5]dec-3-ene and 2,6,9,10,10-pentamethyl-6,7-epoxy-1-oxa-spiro[4.5]decane, useful as intermediate compounds in the preparation of spirane derivatives (II), in accordance with one of the objects of the present invention. The first two of the above mentioned compound may be used, in a one step process, as starting material for preparing 2,6,10,10-tetramethyl-1-oxa-spiro[4.5]decan-6-ol [$R^1 = H$ in formula (II)] as following:

2,6,10,10-tetramethyl-1-oxa-spiro[4.5]dec-3-en-6-ol can be converted into the desired alcohol by means of a catalytic haydrogenation; and 6,7-epoxy-2,6,10,10-tetramethyl-1-oxa-spiro[4.5]-decane can be reduced by means of lithiumaluminium hydride to give the desired alcohol.

Due to the presence of several chirality centres in the molecule, namely at carbon atoms 2, 5 and 6 of the spiro[4.5]decane skeleton, compounds (II) may exist in the form of at least one of the following stereoisomers:

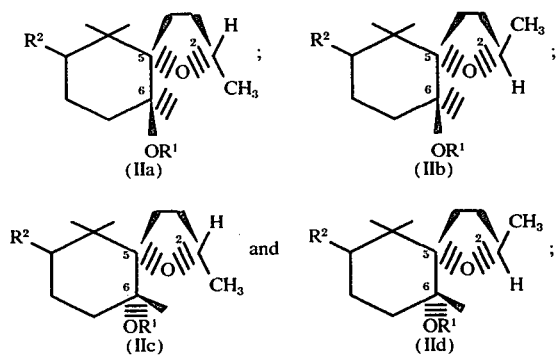

The C(6)-OR$^1$ bond can in fact possess a cis or trans configuration relative to the C(5)-O bond of the heterocycle. This fact may be visualized by means of formulae pairs (IIa) and (IIc), and (IIb) and (IId), respectively.

Moreover the methyl group at position 2 can also possess a cis or trans configuration relative to, for example, the C(5) – C(6) bond of the cyclohexane ring. This isomerism can be visualized by means of formulae pairs (IIa) and (IIb), and (IIc) and (IId), respectively.

All the above stereoisomers can be isolated in their pure state by means of a combination of several techniques such as fractional distillation, crystallisation and preparative vapour phase chromatography. A detailed description of the separation procedure applied to 2,6,10,10-tetramethyl-1-oxa-spiro[4.5]decan-6-ol and its corresponding acetate is given in Example 1.

For practical and economical reasons however, such a separation procedure is generally not necessary. Compounds (II) are most commonly used, in accordance with the present invention, as mixtures of "C(2)-epimers", i.e. as mixtures of stereoisomers (IIa) and (IIb) or stereoisomers (IIc) and (IId), respectively

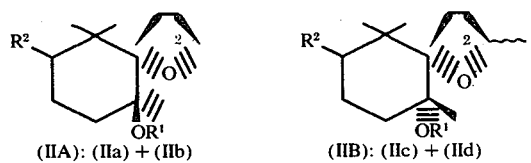

or even as mixtures comprising stereoisomers (IIa), (IIb), (IIc) and (IId).

Although it has been observed that in most of the applications the said mixtures and their individual constituents can develop analogous organoleptic effects, certain olfactive or gustative disparities have been observed.

Alcohol (IIA) for example ($R^1 = H$ in formula IIA) develops a particularly powerful woody and earthy odour whereas alcohol (IIB) possesses a more diffused woody note combined with a slightly flowery nuance. Ester derivatives, more precisely acetates (IIA) and (IIB) ($R^1$ = acetyl in formulae IIA and IIB) also differ one from the other, (IIB) presenting a more developed flowery note.

When acetate (IIA) is used as flavouring ingredient, it can be characterized by its woody, amber-like and cedar-like taste, whereas acetate (IIB) develops a more diffused woody and slightly flowery taste, reminiscent in certain cases of that of ionones.

In accordance with one of the embodiments of the present invention, compounds (II) can be prepared starting from 1-(2,6,6-trimethyl-cyclohex-1-enyl)-butan-1,3-diol when $R^2$ is a hydrogen atom or 1-(2,5,6,6-tetramethyl-cyclohex-1-enyl)-butan-1 3 diol when $R^2$ is methyl (III) as illustrated hereinbelow:

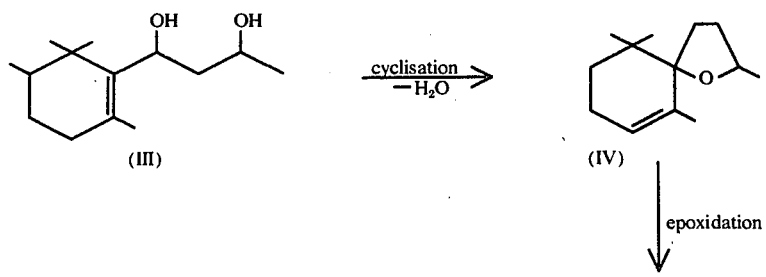

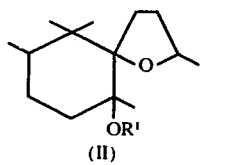 (II) ⇐ 1) reduction  2) esterification  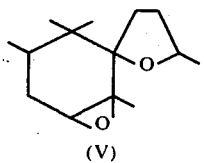 (V)

The first step of the above process, which formally consists in the cyclisation of (III) and the concomitant elimination of a molecule of water, can be effected in the presence of an acidic reagent. The alkali metal salt of a polybasic acid such as sodium or potassium hydrogenosulfate can be conveniently used to this end, as well as a mineral or organic acid, e.g. sulfuric, phosphoric, hydrochloric or p-toluene-sulfonic acid. The said cyclisation can also be carried out in the presence of an acidic diatomaceous earth.

In accordance with a preferred embodiment of the above process, the said cyclisation can be effected by either a. directly mixing the diol (III) with the alkali metal hydrogenosulfate and subsequently heating the thus obtained mixture at a temperature comprised between about 50° and 150° C, preferably under reduced pressure, or b. dissolving compound (III) in an inert organic solvent such as an aromatic hydrocarbon, toluene or benzene e.g., or a halogenated hydrocarbon, methylene chloride or chloroform e.g., and subsequently heating the above solution at the boiling temperature, in the presence of alkali metal hydrogenosulfate.

The epoxidation of compound (IV) can be effected by means of an organic peracid, in accordance with known techniques. Suitable peracids are performic, peracetic, trifluoroperacetic, perbenzoic, monochlorbenzoic or perphthalic acids.

The said epoxidation is moreover carried out in the presence of an organic solvent such as chloroform, methylene chloride, trichlorethylene or dichlorethane e.g. Peracetic acid in methylene chloride is preferably used, in the presence of a buffering agent such as sodium or potassium formate, acetate, propionate, butyrate, oxalate, citrate or tartrate e.g., sodium acetate being the preferred one.

Peracetic acid can also be prepared in situ from the action of hydrogen peroxide on acetic acid, in accordance with the method described in H. O. House, Modern Synthetic Reactions, 2nd ed. Benjamin Inc (1972), p. 293.

The reduction of compound (V) consists in the ring opening of the oxiran moiety of the molecule to give the corresponding tertiary alcohol ($R^1$= H in formula II). The said reduction can be performed in accordance with usual techniques, for example by means of an alkali metal aluminiumhydride such as lithiumaluminium hydride [see H. O. House, op.cit., p. 103].

The esterification in the thus obtained alcohol can be effected in accordance with the known techniques, for example by means of an acyl halide, preferably an acyl chloride, in the presence of an organic base such as N,N-dimethyl-aniline e.g.

2,6,10,10-Tetramethyl-1-oxa-spiro[4.5]dec-6-yl acetate was prepared as indicated hereinabove, from 2,6,10,10-tetramethyl- 1-oxa-spiro[4.5]decan-6-ol and acetyl chloride. 2,6,10,10-Tetramethyl-1-oxa-spiro[4.5]dec-6-yl formate on the contrary was obtained by treating the above alcohol with formylimidazole, according to the method given in Liebigs Ann. Chem. 655, 95 (1962).

The diol of formula (III) used as starting material in the above process may be obtained for example in accordance with the method described in German Patent Application No. 2,315,640.

In Accordance with another embodiment of the present invention, compounds (II) can be obtained from 2,6,10,10-tetramethyl-1-oxa-spiro[4.5]deca-3,6-diene when $R^2$ is a hydrogen atom and 2,6,9,10,10-pentamethyl-1-oxa-spiro[4.5]deca-3,6 diene when $R^2$ is methyl (VI) as described in the following reaction scheme:

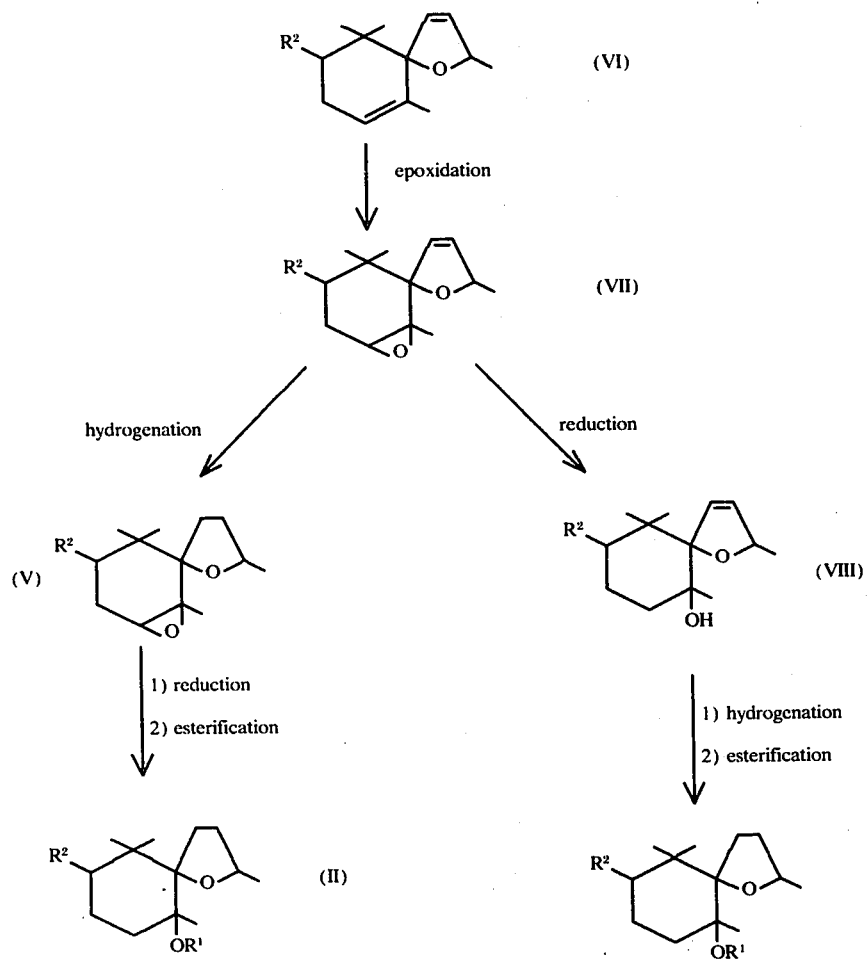

The epoxidation of compound (VI) is effected as described above for compound (IV).

The hydrogenation of both compounds (VII) and (VIII) is carried out in the presence of a metal catalyst, according to the usual techniques. The said hydrogenation may be effected in the presence of platinum oxide, palladium on charcoal or Raney-nickel e.g., and in the presence of an inert organic solvent such as an alcohol, methanol, ethanol or isopropanol e.g., or in the presence of an aliphatic or aromatic hydrocarbon such as hexane, benzene or toluene e.g. The said hydrogenation is preferably carried out by means of palladium on charcoal, in ethanol.

The reduction of compound (VII) is effected as mentioned above for compound (V), i.e. by means of an alkali metal aluminium hydride.

2,6,10,10-Tetramethyl-1-oxa-spiro[4.5]deca-3,6-diene or 2,6,9,10,10-pentamethyl-1-oxa-spiro[4.5]deca-3,6-diene used as starting materials in the above process may be obtained from an acetylenic derivative of formula

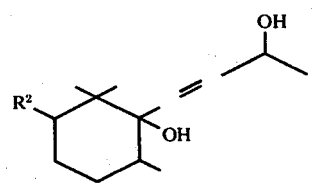

by treating the said derivative with an acidic dehydrating agent, according to the process given in Swiss Pat. No. 544,733.

In accordance with a further embodiment of the present invention compounds (II) can also be prepared from an unsaturated alicyclic alcohol of formula

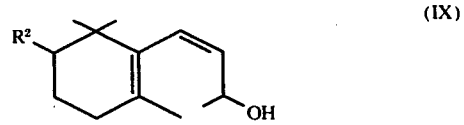

(IX)

by epoxidizing and subsequently subjecting to an acidic treatment said compound (IX) to give a spirane derivative of formula

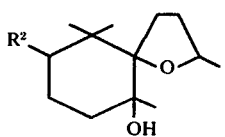

(VIII)

which is finally converted into compound (II) as mentioned hereinabove.

The epoxidation of 4-(2,6,6,-trimethyl-cyclohex-1-enyl)-but-cis 3-ene-2-ol or 4-(2,5,6,6-tetramethyl-cyclohex-1-enyl)-but-cis 3-ene-2-ol (IX) is effected as given above for compound (IV). According to a preferred embodiment of the above process, the said epoxidation is effected by means of peracetic acid in methylene chloride, in the presence of sodium acetate.

The acidic treatment of the product resulting from the epoxidation of compound (IX) may be carried out by means of a mineral or organic acid such as hydrochloric, sulfuric, phosphoric, benzenesulfonic or p-toluenesulfonic acid e.g., or an acidic diatomaceous earth.

The said acidic treatment is moreover effected in the presence of an inert organic solvent, preferably that of the preceding reaction step, methylene chloride in the present case.

Compound (IX) used as starting material in the above process may be obtained from β-ionone, in accordance with the method given in J. Org. Chem. 38, 1247 (1973).

The present invention will be better illustrated by the following Examples wherein the temperatures are given in degrees centigrade and the abbreviations have the meaning common in the art.

EXAMPLE 1

2,6,10,10-Tetramethyl-1-oxa-spiro[4.5]decan-6-ol

Method A:

i. A mixture of 20 g (0.094 M) of 1-(2,6,6-trimethyl-cyclohex-1-enyl)-butan-1,3-diol and 10 g of $KHSO_4$ was heated at 80°, under 0.1 Torr, in a reaction vessel equipped with a lateral distillation column. After having collected the theoretical amount of water the reaction mixture was heated to 100°–110° and 16.6 g of 2,6,10,10-tetramethyl-1-oxa-spiro [4.5]dec-6-ene (theaspirane) were then distilled, b.p. 70°–90°/0.1 Torr. An analytical sample was purified by fractional distillation, b.p. 32°–33°/0.01 Torr.

IR (neat) : 2960, 1450, 1380, 1080, 1000 $cm^{-1}$

NMR ($CCl_4$) : 0.82 and 0.88 (6H, 2s); 1.18 (3H, d, J = 6 cps); 1.65 (3H, d, J = ca. 2 cps); 4.00 (1H, broad m); 5.18 (1H, broad m) δ ppm MS : $M^+$ = 194; m/e = 179 (1), 138 (100), 123 (7), 109 (11), 96 (18), 82 (27).

The cyclisation of 1-(2,6,6-trimethyl-cyclohex-1-enyl)-butane-1,3-diol can also be carried out as indicated hereinbelow:

85 g (0.4 M) of the above diol in 250 ml of $CHCl_3$ were heated to reflux in the presence of 4.25 g of $KHSO_4$, in a reaction vessel equipped with a water-separator. Once the theoretical amount of water has been collected, a new portion of 4.25 g of $KHSO_4$ was added and the reaction mixture was subjected to a fractional distillation to give 56 g (ca. 72%) of theaspirane, b.p. 103°–105°/11 Torr.

ii. 12 ml of a 40% solution of peracetic acid were added dropwise, under stirring, to a cold (0°–5°) mixture of 11.7 g (0.06 M) of theaspirane — see letter i —, 7.4 g of anhydrous sodium acetate and 100 ml of methylene chloride. The reaction mixture was stirred for 5 hours to 5°–10°, then kept overnight at 10° and finally filtered. The clear liquid thus obtained was then washed with water, neutralized with solid $NaHCO_3$, dried over $Na_2SO_4$ and evaporated to give 11 g of a 70:30 isomeric mixture of 6,7-epoxy-2,6,10,10-tetramethyl-1-oxa-spiro[4.5]decane — isomers A and B — according to the vapour phase chromatography analysis.

Isomers A and B were separated on a larger scale (about 250 g) as follows: 236 g of the epoxidation product of theaspirane were subjected to a fractional distillation on a column filled with glass helices (1 = 40 cm − φ = 2cm). 120.6 g of a fraction having b.p. 51°–55°/0.1 Torr and containing 98% of isomer A were first collected, followed by 16.7 g of a fraction having 70°–75°/0.1 Torr and containing 90% of isomer B. This latter product was finally purified by column chromatography (Silicagel - eluant : $CHCl_3$) and subsequent crystallisation in aqueous ethanol. The thus purified isomers present the following analytical data:

Isomer A : B.p. 51°–52°/0.1 Torr

IR (neat) : 2960, 1450, 1380, 1085, 1045, 1010, 970, 890 $cm^{-1}$

NMR ($CCl_4$) : 0.74 and 0.82 (6H, 2s); 1.20 (3H, s); 1.19 (3H, d, J = 5cps); 1.85 (5H, m); 2.88 (1H, broad t); 4.03 (1H broad m) δ ppm MS : $M^+$ = 210 (24); m/e = 154 (61), 126 (66), 125 (50), 111 (32), 85 (27), 69 (46), 55 (59), 43 (100), 41 (49).

Isomer B : M.p. 40°

IR ($CCl_4$) : 2980, 1450, 1380, 1360, 1090, 1010, 900 $cm^{-1}$

NMR($CCl_4$) : 0.75 (3H, s); 0.90 (3H, s); 1.21 (3H, s and 3H, d, J = 7 cps); 2.82 (1H, broad t); 3.94 (1H, broad m) δ ppm MS : $M^+$ = 210 (19); m/e = 154 (58), 126 (56), 125 (39), 111 (26), 70 (27), 69 (38), 55 (53), 43 (100), 41 (41).

iii. a solution of 3.74 g (0.018 M) of the epoxide obtained sub letter ii — isomer A — in 25 ml of ether were added dropwise to a suspension of 1 g of $LiAlH_4$ in 25 ml of ether, kept at 30°–35°. After the addition of the reactants, the obtained mixture was stirred for 3 hours to 35°, then 2 days at room temperature. After the addition of 25 ml of water, washing, drying, evaporation of the organic layer and fractional distillation of the obtained residue, 3.0 g (ca. 80%) of 2,6,10,10-tetramethyl-1-oxa-spiro[4.5]decan-6-ol were isolated — isomer A.

The isomeric alcohol — B — was prepared as indicated hereinabove from the corresponding epoxide — isomer B.

Isomer A : B.p. 58°–59°/0.5 Torr

IR (neat) : 3490, 2940, 1480, 1380, 1080, 1005, 985 $cm^{-1}$

NMR ($CCl_4$) : 0.82 (3H, s); 1.10 (6H, 2s); 1.15 (3H, d); 1.80 (1H, s); 4.00 (1H, broad m) δ ppm MS : $M^+$ = 212 (4); m/e = 126 (89), 109 (29), 86 (70), 85 (100), 84 (51), 69 (46), 55 (28), 43 (93), 41 (44).

Isomer B : B.p. 38°/0.1 Torr

IR (neat) : 3560, 2920, 1455, 1375, 1165, 1075, 965 $cm^{-1}$

NMR ($CCl_4$) : 0.89 (3H, s); 0.96 (3H, s); 1.17 (3H, s); 1.23 (3H, d, J = 7 cps); 4.10 (1H, broad m) δ ppm MS : M⁺ = 212 (2); m/e = 126 (74), 109 (19), 86 (53), 85 (100), 84 (37), 71 (20), 69 (27), 43 (70), 41 (27).

Both isomers A and B are in fact mixtures of "C(2)-epimers" — see preceding part of the specification — which have been individually characterized as indicated hereinafter.

123 g of 2,6,10,10-tetramethyl-1-oxa-spiro[4.5] dec-6-ene (theaspirane) — prepared sub letter i — were subjected to a preparative vapour phase chromatography (CARBOWAX 20 M — 4 m × φ 25 mm — 140° to 175°) to give two portions of 37.5 g and 32.2 g, respectively. The above two fractions were finally purified by means of a fractional distillation and gave 31.5 g and 24.8 g of pure stereoisomers①and②,respectively.

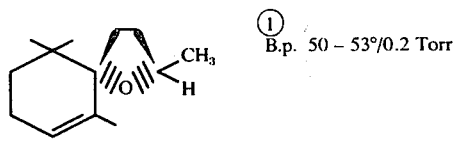

① B.p. 50 – 53°/0.2 Torr

NMR : 0.90 and 0.96 (6H, 2s); 1.28 (3H, d, J = 6 cps); 1.74 (3H, broad s); 4.15 (1H, m); 5.26 (1H, broad s) δ ppm MS : m/e = 139 (10), 138 (100), 109 (13), 96 (21), 83 (14), 82 (33), 55 (10), 43 (12), 41 (12).

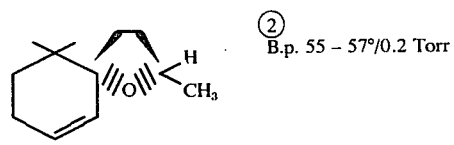

② B.p. 55 – 57°/0.2 Torr

NMR : 0.87 and 1.00 (6H, 2s); 1.28 (3H, d, J = 6 cps); 1.73 (3H, broad s); 4.03 (1H, m), 5.41 (1H, broad t) δ ppm MS : m/e = 139 (10), 138 (100), 109 (14), 96 (23), 83 (15), 82 (31), 55 (10), 43 (10), 41 (13).

30.3 g of theaspirane① were epoxidized as described sub letter ii to yield, after work up, 32 g of a 9:1 epimeric mixture of epoxides③ and ④. The above material was then subjected to a fractional distillation, using a column filled with glass helices ( l = 40 cm – φ 2 mm), to give 19.8 g of a fraction having b.p. 50° – 55°/0.2 Torr and 2.2 g of a fraction having b.p. 60° – 70°/0.2 Torr, respectively. The first of the above two fractions was finally crystallized from aqueous ethanol and gave 4.2 g of pure 6,7-epoxy-2,6,10,10-tetramethyl-1-oxa-spiro [4.5] decane (stereoisomer③).

1.5 g of the second fraction were subjected to a column chromatography (silicagel - hexane/ethyl acetate) to yield 0.46 g of pure stereoisomer④ an oily colourless liquid.

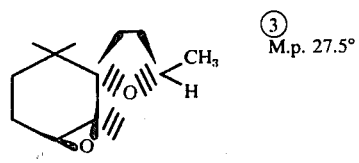

③ M.p. 27.5°

NMR : 0.79 and 0.89 (6H, 2s); 1.26 (3H, d, J = 6 cps); 1.33 (3H, s); 3.07 (1H, broad t); 4.06 (1H, m) δ ppm MS : M⁺ = 210 (24); m/e = 154 (59), 126 (75), 125 (52), 111 (35), 70 (33), 69 (42), 55 (62), 43 (100), 41 (57).

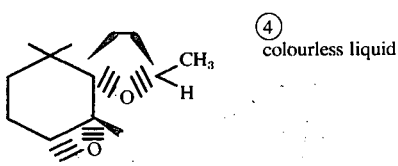

④ colourless liquid

NMR : 0.81 and 0.95 (6H, 2s); 1.25 (3H, d, J = 6 cps); 1.40 (3H, s), 2.99 (1H, broad t); 4.28 (1H, m) δ ppm MS : M⁺ = 210 (17); m/e = 154 (36), 126 (81), 125 (43), 111 (31), 70 (37), 69 (44), 55 (52), 43 (100), 41 (49).

23.2 g of theaspirane② were epoxidized as described hereinabove to yield 24.5 g of a 3:2 epimeric mixture of epoxides⑤ and ⑥. The above mixture was then subjected twice to a fractional distillation, using a column filled with glass helices — see above — to give 11.9 g of an oily material having b.p. 53° –55°/0.2 Torr, which was finally purified by means of a distillation on a spinning band column. There were thus obtained 1.3 g of pure stereoisomer⑤.

10 g of a fraction having b.p. 65° –70°/0.2 Torr, resulting from the first distillation, were crystallized twice from aqueous ethanol to yield 1.4 g of pure stereoisomer⑥.

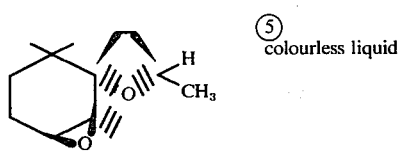

⑤ colourless liquid

NMR : 0.90 and 0.93 (6H, 2s); 1.28 (3H, d, J = 6 cps); 1.31 (3H, s); 3.04 (1H, d, J = 2 cps); 4.16 (1H, m) δ ppm MS : M⁺ = 210 (26); m/e = 1.54 (64), 126 (45), 125 (34), 111 (27), 85 (27), 69 (38), 55 (60), 43 (100), 41 (50).

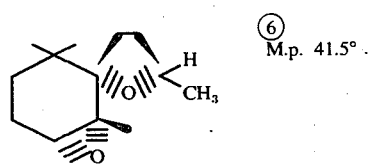

⑥ M.p. 41.5°

NMR : 0.76 and 0.90 (6H, 2s); 1.30 (3H, d, J = 6 cps); 1.32 (3H, s); 2.98 (1H, broad s); 3.90 (1H, m) δ ppm MS : M⁺ = 210 (17); m/e = 1.54 (70), 139 (33), 126 (56), 112 (36), 70 (31), 69 (39), 55 (61), 43 (100), 41 (53).

Pure epoxides ③, 4, 5 and ⑥ were then converted into the corresponding alcohols by means of LiAlH₄ as given sub letter iii, to yield pure stereoisomers ⑦, ⑧,⑨ and ⑩, respectively.

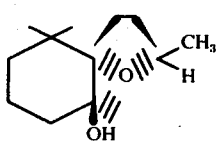 ⑦ colourless liquid

NMR : 0.87 and 1.15 (6H, 2s); 1.19 (3H, s); 1.21 (3H, d, J = 6 cps); 4.1 (1H, m) δ ppm
MS : M⁺ = 212 (3); m/e = 126 (82), 86 (55), 85 (100), 84 (41), 71 (24), 69 (33), 55 (24), 43 (86), 41 (36).

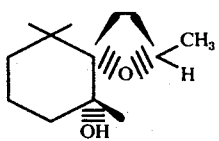 ⑧ colourless liquid

NMR : 0.94 and 0.99 (6H, 2s); 1.19 (3H, s); 1.25 (3H, d, J = 6 cps); 4.13 (1H, m) δ ppm
MS : M⁺ = 212 (2); m/e = 126 (78), 86 (55), 85 (100), 84 (40), 71 (21), 70 (22), 69 (28), 43 (80), 41 (35).

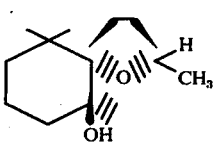 ⑨ colourless liquid

NMR : 0.9 and 1.06 (6H, 2s); 1.14 (3H, s); 1.22 (3H, d, J = 6 cps); 4.05 (1H, m) δ ppm
MS : M⁺ = 212 (3); m/e = 126 (77), 109 (25), 86 (49), 85 (100), 84 (39), 69 (36), 55 (24), 43 (89), 41 (36).

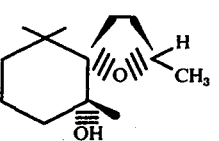 ⑩ colourless liquid

NMR : 0.92 and 0.99 (6H, 2s); 1.25 (3H, d, J = 6 cps); 1.26 (3H, s); 4.12 (1H, m) δ ppm
MS : M⁺ = 212 (1); m/e = 126 (75), 86 (51), 85 (100), 84 (38), 71 (21), 69 (29), 55 (20), 43 (78), 41 (32).

The above pure alcohols were finally converted into the corresponding acetates, by means of acetyl chloride and N,N-dimethylaniline as described in Example 3 hereinafter. Pure stereoisomers ⑪, ⑫, ⑬ and ⑭ respectively were thus obtained.

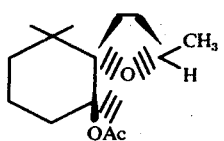 ⑪ M.p. 62°

NMR : 0.88 and 1.08 (6H, 2s); 1.23 (3H, d, J = 6 cps); 1.48 (3H, s); 1.99 (3H, s); 4.14 (1H, m) δ ppm
MS : M⁺ = 254 (1); m/e = 194 (29), 138 (33), 126 (99), 125 (46), 85 (27), 69 (59), 55 (30), 43 (100), 41 (41).

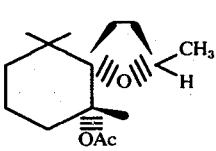 ⑫ colourless, semi-crystalline

NMR : 0.96 (6H, s); 1.24 (3H, d, J = 6 cps); 1.55 (3H, s); 2.0 (3H, s); 4.24 (1H, m) δ ppm
MS : M⁺ = 254 (1); m/e = 194 (27), 138 (25), 126 (100), 125 (50), 85 (21), 69 (64), 55 (32), 43 (97), 41 (42).

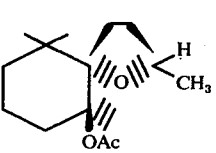 ⑬ M.p. 35.5°

NMR : 0.90 and 0.99 (6H, 2s); 1.27 (3H, d, J = 6 cps); 1.44 (3H, s); 2.0 (3H, s); 4.06 (1H, m) δ ppm
MS : M⁺ = 254 (2); m/e 194 (31), 128 (27), 126 (88), 125 (35), 85 (29), 69 (48), 55 (27), 43 (100), 41 (36).

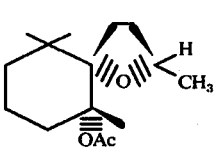 ⑭ M.p. 47°

NMR : 0.94 and 1.0 (6H, 2s); 1.25 (3H, d, J = 6 cps); 1.60 (3H, s); 2.01 (3H, s); 4.14 (1H, m) δ ppm
MS : M⁺ = 254 (1); m/e 194 (28), 128 (23), 126 (98), 125 (39), 85 (31), 69 (56), 55 (30), 43 (100), 41 (40).

All the above NMR spectra were carried out on a 90 MHz apparatus, in $CDCl_3$.

Method B:
i. 22.7 g (0.12 M) of a 40% solution of peracetic acid were added to a mixture of 19.2 g (0.1 M) of 2,6,10,10-tetramethyl-1-oxa-spiro[4.5]deca-3,6-diene, 12.3 g of anhydrous sodium acetate and 100 ml of methylene chloride as indicated above — see method A; letter ii —. After the usual treatments of washing, drying and distillation, there were isolated 9.2 g of a product having b.p. 45°–47°/0.1 Torr and containing 90% of 6,7-epoxy-2,6,10,10-tetramethyl-1-oxa-spiro[4.5]dec-3-ene in accordance with the vapour phase chromatography analysis.

A new distillation of the above-material finally gave 5.7 g of the desired epoxide, b.p. 47°/0.1 Torr.
IR (neat) : 2970, 1460, 1380, 1360, 1100, 1075, 910, 760 cm⁻¹
NMR($CCl_4$) : 0.70 (3H, s); 0.72 (3H, s); 0.86 (3H, s); 1.13 (3H, s); 1.23 (3H, d, J = 7 cps); 1.27 (3H, d, J = 7 cps); 1.85 (2H, broad m); 2.92 (1H, t); 4.90 (1H, m); 5.75 (2H, s); 5.78 (2H, s) δ ppm
MS : M⁺ = 208 (1); m/e = 137 (39), 126 (68), 123 (46), 111 (22), 109 (38), 95 (23), 55 (20), 43 (100), 41 (23).

ii. 3.12 g of the above epoxide in 50 ml of ethanol were hydrogenated in the presence of 312 mg of palladium on charcoal. After 340 ml of hydrogen have been consumed, the reaction mixture was filtered, evaporated and finally subjected to a fractional distillation to give 2.0 g (64%) of 6,7-epoxy-2,6,10,10-tetramethyl-1-oxa-spiro[4.5]decane — isomer A; see method A, letter ii —, b.p. 51°/0.1 Torr.

iii. 1.68 g of the above epoxide were subjected to a reduction carried out by means of 455 mg of LiAlH$_4$ in accordance with the process described in method A — letter iii — and gave 1.50 g (ca. 90%) of 2,6,10,10-tetramethyl-1-oxa-spiro[4.5]decan-6-ol — isomer A; see method A, letter iii.

2,6,10,10-tetramethyl-1-oxa-spiro[4.5]deca-3,6-diene used as starting material in the above process was prepared from 1-hydroxy-2,6,6-trimethyl-1-(3-hydroxy-but-1-yne-1-yl)-cyclohexane, by treating this latter compound with a 30% aqueous solution of H$_2$SO$_4$, in accordance with the method described in Swiss Patent No 544733.

IR (neat) : 2990–2840, 1470, 1380, 1350, 1115, 1080, 980 cm$^{-1}$

MS : m/e = 193, 136, 121, 93, 77, 53, 43, 41.

Method C:

i. 2.08 g (0.01 M) of 6,7-epoxy-2,6,10,10-tetramethyl-1-oxa-spiro[4.5]dec-3-ene — see method B, letter i — were reduced by means of 570 mg (0.015 M) of LiAlH$_4$ in accordance with the above process. After the usual treatments of washing, drying and evaporation, the fractional distillation of the obtained residue gave 1.9 g (ca. 90%) of 2,6,10,10-tetramethyl-1-oxa-spiro[4.5]dec-3-ene-6-ol, b.p. 80°–90°/0.1 Torr.

IR (CCl$_4$) : 3620, 3490, 3070, 2930, 1455, 1370, 1190, 1080, 995, 935, 870, 705 cm$^{-1}$

NMR(CCl$_4$) : 0.80 (3H, s); 1.07 (6H, 2s); 1.20 and 1.22 (3H, 2d, J = 7cps); 4.82 (1H, qd, J = 7cps); 5.82 (2H, s) δ ppm MS : M$^-$ = 210 (4); m/e = 149 (38), 126 (63), 125 (30), 123 (29), 109 (50), 83 (22), 69 (29), 43 (100), 41 (21).

2,6,10,10-Tetramethyl-1-oxa-spiro[4.5]dec-3-ene-6-ol is a new compound, as well as its acetate derivative. Both compounds are characterized by their woody and balsamic odour, reminiscent in certain cases to that of patchouli. They can advantageously be used in perfumery or in the flavour industry as perfuming and/or flavouring ingredients.

2,6,10,10-Tetramethyl-1-oxa-spiro[4.5]dec-3-en-6-yl acetate possesses the following analytical data:

IR (neat) : 1730 cm$^{-1}$

NMR (CDCl$_3$) : 0.83 (3H, s); 1.11 (3H, s); 1.25 (3H, d, J = 7 cps); 1.40 (3H, s); 1.98 (3H, s); 4.88 (1H, m); 5.86 (2H, m) δ ppm MS : M$^+$ = 252 (2); m/e = 209 (22), 127 (28), 126 (11), 123 (40), 109 (81), 83 (12), 69 (29), 55 (11), 43 (100), 41 (18).

ii. 53 mg of 2,6,10,10-tetramethyl-1-oxa-spiro[[4.5]-dec-3-ene-6-ol in 5 ml of ethanol were subjected to a hydrogenation in the presence of 5 mg of palladium on charcoal. After the absorbtion of 5 ml of hydrogen, the reaction mixture was treated as described in method B — letter ii — to give 45 mg of a material containing 80% of the desired alcohol — isomer A; see method A, letter iii — and 20% of starting material according to the vapour phase chromatography analysis.

Method D:

i. 2.28 g (ca. 0.012 M) of a 40% solution of peracetic acid containing 2% of sodium acetate were added dropwise to a cold — 0° — mixture of 2.33 g (0.012 M) of 4-(2,6,6-trimethyl-cyclohex-1-enyl)-but-cis-3-ene-2-ol, 1.73 g (0.018 M) of sodium acetate and 70 ml of methylene chloride. After the addition of the reactants, the reaction mixture was stirred for 15 hours at room temperature and finally filtered. The clear liquid thus obtained was then successively treated with 2 portions of a 10% aqueous solution of NaHCO$_3$ and a saturated solution of NaCl, and then dried over Na$_2$SO$_4$. After evaporation of the volatile parts, the thus obtained residue was purified by means of a column chromatography (Silicagel — eluant: cyclohexane/ethyl acetate 7 : 3) to give 0.53 g of starting material and 1.76 g of an unidentified epoxy-derivative (ca. 90% yield).

ii. The above epoxy-derivative was then treated with 50 ml of methylene chloride, in the presence of 0.07 g of p-toluenesulfonic acid and in a nitrogen atmosphere. After having been stirred for 24 hours the reaction mixture was neutralized, washed, dried and evaporated as indicated herein above — see letter i — and the distillation of the obtained residue gave 1.58 g (ca. 90%) of 2,6,10,10-tetramethyl-1-oxa-spiro[4.5]dec-3-ene-6-ol.

iii. 1.54 g (ca. 0.007 M) of the above alcohol were subjected to a hydrogenation in the presence of palladium on charcoal as indicated above — see method C, letter ii — 1.08 g (55%) of 2,6,10,10-tetramethyl-1-oxa-spiro[4.5]decan-6-ol — isomer A; see method A, letter iii — were thus isolated.

EXAMPLE 2

2,6,10,10-Tetramethyl-1-oxa-spiro[4.5]dec-6-yl formate 0.4 g (0.002 M) of 2,6,10,10-tetramethyl-1-oxa-spiro[4.5]decan-6-ol — isomer A; see Example 1 — were intimately mixed with 0.5 g (0.005 M) of freshly sublimated formylimidazole and then kept for 2 days at room temperature. The reaction mixture was then extracted with ether and the organic layer washed, dried, evaporated and finally subjected to a fractional distillation to give 0.3 g of a product having b.p. 70°–80°/0.5 Torr and containing 60% of the desired ester. An analytical sample was purified by vapour phase chromatography.

IR (neat) : 2970, 1730, 1200, 1170, 1080 cm$^{-1}$

NMR (CDCl$_3$) : 0.88 (3H, s); 1.08 (3H, s); 1.22 (3H, d, J = 6 cps); 1.48 (3H, broad s); 4.15 (1H, broad m); 8.12 (1H, s) δ ppm MS : (M + 1)$^+$ = 241 (2); m/e = 194 (34), 138 (87), 126 (62), 125 (95), 82 (30), 69 (100), 55 (42), 43 (61), 41 (56).

EXAMPLE 3

2,6,10,10-Tetramethyl-1-oxa-spiro[4.5]dec-6-yl acetate 5.9 g (0.079 M) of acetyl chloride were added over 30 minutes at 20° to a mixture of 2,6,10,10-tetramethyl-1-oxa-spiro[4.5]decan-6-ol — isomer A; see Example 1 — and 10.9 g of N,N-dimethylaniline. After having been kept for 2 days at room temperature the reaction mixture was heated to reflux during 3 hours, then cooled and treated with 50 ml of ether. The reaction mixture was then filtered and the clear filtrate thus obtained poured onto crushed ice and finally acidified with a 10% aqueous solution of H$_2$SO$_4$. The organic layer was then washed with NaHCO$_3$ in water, dried, evaporated and subjected to a fractional distillation to give 2.5 g of a product having b.p. 90°–100°/0.1 Torr. After crystallisation in aqueous ethanol 1.9 g (75%) of the desired ester were isolated — isomer A.

The isomeric acetate B was obtained from the corresponding alcohol — isomer B; see Example 1 — as indicated hereinabove.

Isomer A: M.p. 55°–56°

IR (CHCl$_3$) : 2950, 1730, 1360, 1240, 1160, 1070 cm$^{-1}$

NMR (CDCl$_3$) : 0.87 (3H, s); 1.07 (3H, s); 1.22 (3H, d, J = 6 cps); 1.44 (3H, s); 1.95 (3H, s); 4.10 (1H, broad m) δ ppm Ms : (M + 1)$^+$ = 255 (2); m/e = 194 (29), 138 (26), 126 (100), 125 (38), 85 (24), 69 (45), 55 (22), 43 (85), 41 (28).

Isomer B: M.p. 46°

IR (CHCl$_3$) : 2980, 1720, 1375, 1255, 1090, 905 cm$^{-1}$

NMR (CDCl$_3$) : 0.93 (3H, s); 0.98 (3H, s); 1.24 (3H, d, J = 7 cps); 1.57 (3H, s); 1.98 (3H, s); 4.14 (1H, broad m) δ ppm Ms : M$^+$ = 254 (1); m/e = 194 (32), 138 (30), 126 (97), 125 (53), 85 (29), 69 (67), 55 (31), 43 (100), 41 (41).

EXAMPLE 4

2,6,10,10-Tetramethyl-1-oxa-spiro[4.5]dec-6-yl propionate 2.17 g (0.01 M) of 2,6,10,10-tetramethyl-1-oxa-spiro[4.5]decan-6-ol — isomer A; see Example 1 — were treated with a mixture of 12.1 g (0.10 M) of N,N-dimethylaniline and 4.62 g (0.05 M) of propionyl chloride as indicated in Example 3 to give 1.7 g (63%) of the desired ester, b.p. 100°–110°/0.5 Torr.

IR (neat) : 2950, 1730, 1460, 1370, 1190, 1160, 1070, 1010 cm$^{-1}$

NMR (CDCl$_3$) : 0.87 (3H, s); 1.07 (3H, s and 3H, t, J = 7 cps); 1.21 (3H, d, J = 6 cps); 1.43 (3H, s); 4.12 (1H, broad m) δ ppm MS : (M + 1)$^+$ = 269 (2); m/e = 194 (36), 138 (28), 126 (100), 125 (38), 85 (25), 69 (46), 57 (35), 43 (52), 41 (29).

EXAMPLE 5

2,6,10,10-Tetramethyl-1-oxa-spiro[4.5]dec-6-yl butyrate 2.12 g (0.01 M) of 2,6,10,10-tetramethyl-1-oxa-spiro[4.5]decan-6-ol — isomer A; see Example 1 — were treated with a mixture of 12.1 g (0.1 M) of N,N-dimethylaniline and 5.3 g (0.05 M) of butyryl chloride as indicated in Example 3 — except heating at 100° for 3 hours — to give 1.6 g (57%) of the desired ester, b.p. 120°/0.5 Torr.

IR (neat) : 2960, 1720, 1450, 1370, 1180, 1150, 1070, 1000 cm$^{-1}$

NMR (CDCl$_3$) : 0.88 (3H, s); 1.08 (3H, s); 1.10 (3H, t); 1.22 (3H, d, J = 6 cps); 1.45 (3H, s); 4.12 (1H, broad m) δ ppm MS : (M + 1)$^+$ = 283 (2); m/e = 211 (24), 194 (41), 138 (30), 126 (100), 125 (40), 71 (29), 69 (48), 43 (76), 41 (36).

EXAMPLE 6

2,6,10,10-Tetramethyl-1-oxa-spiro[4.5]dec-6-yl isobutyrate 2.12 g (0.01 M) of 2,6,10,10-tetramethyl-1-oxa-spiro[4.5]decan-6-ol — isomer A; see Example 1 — were treated with a mixture of 12.1 g (0.1 M) of N,N-dimethylaniline and 5.3 g (0.05 M) of isobutyryl chloride as indicated in Example 5 to give 0.3 g (ca. 11%) of the desired ester, b.p. 110°/0.5 Torr.

IR (neat) : 2960, 1725, 1470, 1380, 1200, 1150, 1080, 1010 cm$^{-1}$

NMR (CDCl$_3$) : 0.88 (3H, s); 1.09 (3H, s); 1.17 and 1.19 (6H, 2s); 1.20 (3H, d, J = 6 cps); 1.43 (3H, s); 4.13 (1H, broad m) δ ppm MS : (M + 1)$^+$ = 283 (2); m/e = 194 (42), 138 (33), 126 (94), 125 (44), 71 (27), 69 (51), 55 (28), 43 (100), 41 (43).

EXAMPLE 7

A black tea infusion possessing a relatively bland taste was prepared from 6 g of commercial black tea leaves and 1 liter of boiling water. After few minutes the above infusion was poured into small cups, at a rate of 30 ml per cup. "Test" samples were then prepared by adding to each cup of hot tea 0.06 ml of a 0.001% solution of 2,6,10,10-tetramethyl-1-oxa-spiro[4.5]decan-6-ol — isomer A; see Example 1 — in 95% ethyl alcohol. A "control" sample was obtained by adding 95% ethyl alcohol to the hot tea, in the same proportions.

"Test" and "control" samples were then subjected to the evaluation of a panel of flavour experts who unanimously declared that the "test" samples possessed a particularly pleasant woody character when compared to the unflavoured material.

Analogous organoleptic effects were obtained, however less pronounced, by replacing the above alcohol by its B isomer — see Example 1 —. Similar effects were observed by using in the same proportion 2,6,9,10,10-pentamethyl-1-oxa-spiro[4.5]decan-6-ol instead of the above mentioned tetramethyl derivative.

EXAMPLE 8

A commercial mushroom soup was flavoured with 2,6,10,10-tetramethyl-1-oxa-spiro[4.5]decan-6-ol — isomer A; see Example 1 — in the proportions of 0.03 mg of the above alcohol per kg of foodstuff: "test" sample. The thus flavoured soup was then compared to an unflavoured material by a panel of experts who declared that the "test" sample possessed a well distinct woody and earthy note.

The above aromatization procedure was then repeated, by replacing 2,6,10,10-tetramethyl-1-oxa-spiro[4.5]decan-6-ol by its corresponding acetate — isomer A; see Example 3. In that case it was found that the flavoured foodstuff possessed an improved woody character together with a pleasant cedar-like nuance.

EXAMPLE 9

To 1 liter of an acidulous sugar syrup (prepared by diluting 650 g of sucrose and 10 ml of a 50% aqueous solution of citric acid in 1000 ml of water), flavoured with lemon oil in the proportion of 30 g of the said oil per 100 l of syrup, there was added 1 ml of a 0.1% ethanolic solution of 2,6,10,10-tetramethyl-1-oxa-spiro[4.5]dec-6-yl acetate — isomer A; see Example 3 — to give the "test" sample. The thus flavoured syrup was then compared to a material containing 95% ethyl alcohol in the proportions given hereinabove ("control" sample) by a panel of experts who declared that the "test" beverage possessed a more marked and more pleasant woody note.

By replacing the above acetate by its B isomer — see Example 3 — analogous effects were achieved. The observed gustative note however was more diffused and possessed moreover a flowery nuance.

By replacing, in the above aromatization procedure, 2,6,10,10-tetramethyl-1-oxa-spiro[4.5]dec-6-yl acetate by the corresponding formate or propionate — see Example 2 and 4 respectively — analogous effects were observed. In this case however higher proportions were used (about ten times more).

EXAMPLE 10

100 mg of a 0.1% ethanolic solution of 2,6,10,10-tetramethyl-1-oxa-spiro[4.5]decan-6-ol — isomer A; see Example 1 — were sprayed onto 100 g of an "american blend" tobacco mixture. The tobacco thus flavoured was used for the manufacture of "test" cigarettes, the smoke of which was then subjected to organoleptic evaluation by comparison with unflavoured "control" cigarettes. The tobacco used to prepare the "control" cigarettes was preliminary treated with a corresponding amount of 95% ethyl alcohol.

A panel of flavour experts defined the taste of the smoke of the "test" cigarettes as possessing a typical woody and earthy character.

By replacing, in the above flavouring procedure, the above alcohol by the corresponding acetate — isomer A; see Example 3 — in the proportions of 0.3 g of 1% ethanolic solution per 100 g of tobacco, it was declared that the "test" cigarettes possessed a particularly pleasant woody and amber-like character, reminiscent at the same time of that of cedar wood.

By replacing the above acetate by its B isomer — see Example 3 — analogous effects were observed. The thus obtained woody and amber-like note was however more diffused and presented moreover a flowery nuance.

EXAMPLE 11

A base perfume composition for shampooings was prepared by admixing the following ingredients (parts by weight):

| | |
|---|---|
| Phenylethyl alcohol | 130 |
| Ethylenebrassylate | 100 |
| Aspic oil 10 %* | 80 |
| Synthetic geraniol | 80 |
| Synthetic bergamot | 80 |
| Linalyl acetate | 60 |
| Synthetic geranium | 60 |
| Oak moss absolute 10 %* | 60 |
| Patchouli oil | 40 |
| Labdanum resinoid 10 %* | 40 |
| p-ter-Butyl-cyclohexyl acetate | 30 |
| Musk ketone | 30 |
| Coumarin | 30 |
| Terpineol | 30 |
| Methyl-isoeugenol | 30 |
| Rosemary oil | 20 |
| Galbanum oil 10 %* | 20 |
| Isocamphyl-cyclohexanol | 20 |
| Synthetic civet 10 %* | 20 |
| Lavandin absolute, discolourized | 10 |
| Synthetic neroli | 15 |
| Lilial, L. Givaudan & Cie SA | 10 |
| Myrtle oil | 5 |
| Total | 1000 |

*in diethyl phthalate

The above base composition possesses an intense and typical woody note, due to the presence of patchouli oil.

By replacing in the above base the 40 parts of patchouli oil by 80 parts of 2,6,10,10-tetramethyl-1-oxa-spiro[4.5]decan-6-ol, there was obtained a new perfume composition similar to the above base, the woody and balsamic notes thereof being more pronounced.

EXAMPLE 12

A base perfume composition for an after-shave lotion was prepared by admixing the following ingredients (parts by weight):

| | |
|---|---|
| Synthetic bergamot | 120 |
| p-ter-Butyl-cyclohexyl acetate | 100 |
| Methyl-octylacetic aldehyde 10 %* | 80 |
| Synthetic jasmine | 60 |
| Lemon oil | 60 |
| Florida orange oil | 50 |
| "Mousse d'arbre" concrete 10 %* | 50 |
| Lavandin absolute | 40 |
| Clove oil of Madagascar | 40 |
| Galbanum resinoid | 40 |
| Synthetic neroli | 40 |
| Undecylic aldehyde 10 %* | 20 |
| α-Phenylethyl acetate | 20 |
| Cananga oil | 20 |
| Methyl-ionone | 20 |
| Musk ambrette | 20 |
| 2,4-Dimethyl-cyclohex-3-enyl-carbaldehyde 10 %* | 20 |
| Total | 1000 |

*in diethyl phthalate

By adding to 80 g of the above base 10 g of 2,6,10,10-tetramethyl-1-oxa-spiro[4.5]dec-6-yl acetate — isomer A; see Example 3 — there was obtained a new perfume composition possessing a particularly elegant woody character, reminiscent of that of vetiver.

By replacing in the above composition the above acetate by its B isomer — see Example 3 — a similar effect was observed. The thus obtained composition possessed however a more diffused woody note together with a flowery tonality.

EXAMPLE 13

A base perfume composition having a woody odour was prepared by admixing the following ingredients (parts by weight):

| | |
|---|---|
| Synthetic bergamot | 300 |
| Vetyveryl acetate | 150 |
| Florida cedar wood oil | 120 |
| Methyl 2-pentyl-3-oxa-cyclopentyl-acetate | 120 |
| Oak moss absolute 10 %* | 120 |
| Isocamphyl cyclohexanol | 90 |
| Total | 900 |

*in diethyl phthalate

The above base possesses a typical woody character, mainly due to the presence of vetyveryl acetate and cedar wood oil. It is particularly suitable for the preparation of various perfume compositions, for example for those having a "masculine" tonality.

By adding to 90 g of the above base 10 g of 7,6,10,10-tetramethyl-1-oxa-spiro[4.5]dec-6-yl acetate — isomer A; see Example 3 — the woody character of the said base was improved and the thus obtained composition presented a more elegant and more harmonious overall effect.

EXAMPLE 14

2,6,9,10,10-Pentamethyl-1-oxa-spira [4.5] decan-6-ol a. 12 ml of a 40% solution of paracetic acid were added within 1h under stirring to a mixture cooled at 0°–5° of 12.4 g (0.06M) of 2,6,9,10,10-pentamethyl-1-oxa-spira [4.5] deca-3,6-diene, 7.4 g of anhydrous sodium acetate and 100 ml $CH_2Cl_2$. The whole is kept under stirring during 5h at 5°–10°, then overnight at 10° and the mixture was filtered. The clear filtrate, washed with $H_2O$, neutralized by means of $NaHCO_3$ and dried over $Na_2SO_4$, was evaporated to give 10 g of 2,6,9,10,10-pentamethyl-6,7-epoxy-1-oxa-spiro [4.5] dec-3-ene. A gas chromatografy purified sample of this epoxide had the following spectral data:

IR(film) : 3100, 3000, 2960, 2900, 2870, 1445, 1090, 1050, 1040, 1000, 950, 905 $cm^{-1}$ $M^+ = 222$ (7); m/e: 140 (45), 123 (100), 109 (59), 43 (85).

b. 8 g of the product obtained sub letter a) above were dissolved in 100 ml of ethanol and catalytically hydrogenated in the presence of 800 mg of 5% palladium on charcoal. On evaporation and fractional distillation, 8 g of 2,6,9,10,10-pentamethyl-6,7-epoxy-1-oxa-spiro [4.5] decane were obtained. An analytical sample was purified by gas chromatography and showed the following characteristics:

IR(film) 1460, 1380, 1090, 1020 $cm^{-1}$;

MS : $M^+ = 224(8)$; m/e : 139(66), 125(92), 43(100), 41(65).

c. 4.0 g (0.018M) of the above obtained compound (see letter b)) were dissolved in 25 ml of ether and the solution was added at 30°–35° to a suspension of 1 g of $LiAlH_4$ in 25 ml ether. Once the addition is over, the mixture is stirred during 3h at room temperature, then 48h at 20°, whereupon water was added thereto. After separation, washing and drying of the organic phase over $MgSO_4$, followed by distillation of the obtained residue, there were isolated 3.0 g of 2,6,9,10,10-pentamethyl-1-oxa-spiro [4.5] decan-6-ol, the spectral data of which were the following:

IR(film) 3520, 2890, 2950, 2890, 1455, 1380, 1375, 1140, 1085, 1010, 940 $cm^{-1}$;

This product was isolated under the form of a mixture of two isomers (A and B) which could be separated by gas chromatography:

Isomer A

NMR ($CDCl_3$; 90MHz) : 0.91(3H,s); 0.98(3H,s); 0.89(3H,dJ = 5 cps); 1.22(3H,d,J = 6 cps); 1.27(3H,s); 1.53(1H,s); 4.13(1H,m) δppm $M^+$= 226 (<1); m/e: 126(84),

MS : 125(57), 85(100), 69(46).

Isomer B

NMR ($CDCl_3$; 90MHz) : 0.82(3H,s); 0.92(3H,s); 0.84 (3H,d,J = 5 cps); 1.22(3H,d,J = 6 cps); 1.35(3H,s); 1.53(1H,s); 4.11(1H,m) δppm MS : $M^+$ = 226 (<1); m/e: 126(88), 125(86), 85(94), 69(69), 43(100).

2,6,9,10,10-Pentamethyl-1-oxa-spiro [4.5] deca-3,6-diene, used as starting material in step a) hereinabove could be prepared from 1-hydroxy-2,5,6,6-tetramethyl-1-(3-hydroxybut-1-yn-1-yl)-cyclohexane by treating said carbinol with a 30% aqueous solution of $H_2SO_4$ as indicated in Swiss Pat. No. 544,733. The compound possessed moreover very interesting organoleptic properties and consequently could advantageously be used as flavouring and perfuming agents. It develops a very powerful natural fruity, minty character reminiscent of certain perfuming notes typical of black-currant fruits.

EXAMPLE 15

In accordance with the procedure described in Example 3, it was provided to the preparation of 2,6,9,10,10-pentamethyl-1-oxa-spiro [4.5] dec-6-yl acetate. The spectral data of the obtained ester were the following:

IR(film) : 1740, 1465, 1370, 1255, 1095, 1025 $cm^{-1}$;

NMR ($CDCl_3$ 90 MHz) : 0.91(3H,s); 0.98(3H,s); 1.20 (3H,d,J = 6 cps); 1.47(3H,s); 1.98(3H,s); 4.09(1H,m) δppm MS : m/e: 138(88), 137(51), 125(100), 69(81), 43(66).

EXAMPLE 16

A base perfume composition for shampoos was prepared by admixing the following ingredients (parts by weight):

| | |
|---|---|
| Phenylethyl alcohol | 170 |
| Ethylenebrassylate 10%* | 100 |
| Aspic oil | 80 |
| Synthetic geraniol | 80 |
| Synthetic bergamont | 80 |
| Lynalyl acetate | 60 |
| Synethetic geranium | 60 |
| Absolu oak-moss 10%* | 60 |
| Labdanum resinoid 10%* | 40 |
| p-ter-Butyl-cyclohexyl acetate | 30 |
| Musk ketone | 30 |
| Coumarin | 30 |
| Terpineol | 30 |
| Methyl-isoeugenol | 30 |
| Rosmarin oil | 20 |
| Galbanum oil 10%* | 20 |
| Isocamphyl-cyclohexanol | 20 |
| Synthetic Civet 10%* | 20 |
| Synthetic neroli | 15 |
| Lavandin absolute colorless | 10 |
| p-ter-Butyl-α-methyl-dihydrocinnamic aldehyde | 10 |
| Myrtle oil | 5 |
| Total | 1000 |

*in diethyl phthalate

By adding to 95 g of the above composition, 5 g of 2,6,9,10,10-pentamethyl-1-oxa-spiro [4.5] decan-6-ol, a novel composition resulted with an improved pleasant woody, vetyver-like odour character.

What we claim is:

1. A spirane derivative of formula

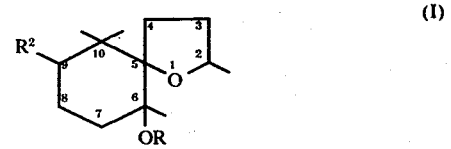

(I)

wherein the symbol R represents an alkanoyl radical containing from 1 to 6 carbon atoms and $R^2$ represents a hydrogen atom or a methyl radical.

2. 2,6,10,10-Tetramethyl-1-oxa-spiro[4.5]dec-6-yl formate.

3. 2,6,10,10-Tetramethyl-1-Oxa-spiro[4.5]dec-6-yl acetate.

4. 2,6,10,10-Tetramethyl-1-oxa-spiro[4.5]dec-6-yl propionate.

5. 2,6,10,10-Tetramethyl-1-oxa-spiro[4.5]dec-6-yl butyrate.

6. 2,6,10,10-Tetramethyl-1-oxa-spiro[4.5]dec-6-yl isobutyrate.

7. 2,6,10,10-pentamethyl-1-oxa-spiro[4.5]dec-6-yl acetate.

* * * * *

UNITED STATES PATENT AND TRADEMARK OFFICE
CERTIFICATE OF CORRECTION

PATENT NO. : 4,014,905
DATED : March 29, 1977
INVENTOR(S) : Werner Skorianetz, Walter Renold, Gunther Ohloff and Karl-Heinrich Schulte-Elte It is certified that error appears in the above-identified patent and that said Letters Patent are hereby corrected as shown below:

Column 17, line 39, "$M^-=$" should read --$M^+=$--.

Column 23, line 49, "2890" first occurrence, should read --2980--.

Signed and Sealed this

Sixth Day of September 1977

[SEAL]

Attest:

RUTH C. MASON
*Attesting Officer*

LUTRELLE F. PARKER
*Acting Commissioner of Patents and Trademarks*